United States Patent [19]
Brumfield et al.

[11] Patent Number: 5,609,592
[45] Date of Patent: Mar. 11, 1997

[54] SPINAL FIXATION SYSTEM

[75] Inventors: David L. Brumfield, South Haven, Mich.; M. Neil Anderson, Memphis, Tenn.; Eduardo R. Luque, Mexico City, Mexico

[73] Assignee: Danek Medical, Inc., Memphis, Tenn.

[21] Appl. No.: 481,045

[22] Filed: Jun. 7, 1995

Related U.S. Application Data

[62] Division of Ser. No. 278, Jan. 4, 1993, Pat. No. 5,527,314.
[51] Int. Cl.$^6$ .................................................. A61B 17/70
[52] U.S. Cl. ................................................. 606/61; 606/72
[58] Field of Search ............................ 606/61, 60, 59, 606/54, 53, 72, 73, 104, 105

[56] References Cited

U.S. PATENT DOCUMENTS

| | | | |
|---|---|---|---|
| 4,662,365 | 5/1987 | Gotzen et al. | 606/59 |
| 5,102,412 | 4/1992 | Rogozinski | 606/61 |
| 5,129,900 | 7/1992 | Asher et al. | 606/61 |
| 5,176,680 | 1/1993 | Vignaud et al. | 606/61 |
| 5,209,752 | 5/1993 | Ashman et al. | 606/61 |

*Primary Examiner*—Guy V. Tucker
*Attorney, Agent, or Firm*—Woodard, Emhardt, Naughton, Moriarty & McNett

[57] ABSTRACT

A spinal implant system for correcting spinal deformities and abnormalities includes an elongated spinal rod configured to be implanted adjacent the spinal column and spanning across several vertebral levels. A number of fixation elements, such as spinal hooks, are provided for engaging vertebrae at a number of vertebral levels. At least some of the fixation elements includes an elongated stem projecting from a vertebra engaging portion. The stems of each of the fixation elements are connected to the spinal rod by way of a rod connector having a one-piece body defining a rod channel adapted to receive the spinal rod therethrough, a stem bore adapted to receive a stem therethrough, and a threaded bore. The stem bore and rod channel intersect to permit contact between the rod and the stem of a fixation element. The threaded bore intersects either the rod channel or the stem bore so that a set screw threaded into the threaded bore bears against the spinal rod or fixation element stem. As the set screw is tightened in the bore, the spinal rod and stem are clamped together to form a rigid construct. The rod channel includes a channel opening to permit top-loading of the rod connector. The fixation element stem may include external threads to receive a threaded fastener for temporarily threading onto the stem when the implant construct is at an initial posterior level above the spine. As the fastener is threaded onto the stem of each fixation element, the instrumentation is drawn down to a lower final level adjacent the vertebrae.

20 Claims, 8 Drawing Sheets

Fig. 1

*(PRIOR ART)*

SPINAL FIXATION SYSTEM

This application is a division of application Ser. No. 08/000,278, filed Jan. 4, 1993, now U.S. Pat. No. 5,527,314.

BACKGROUND OF THE INVENTION

The present invention concerns a spinal fixation system, particularly a system for posterior fixation of the sphere for the treatment of spinal deformities. Specifically, the system contemplates various components interconnected together by way of elongated rods extending along the spinal column.

Figure 1:
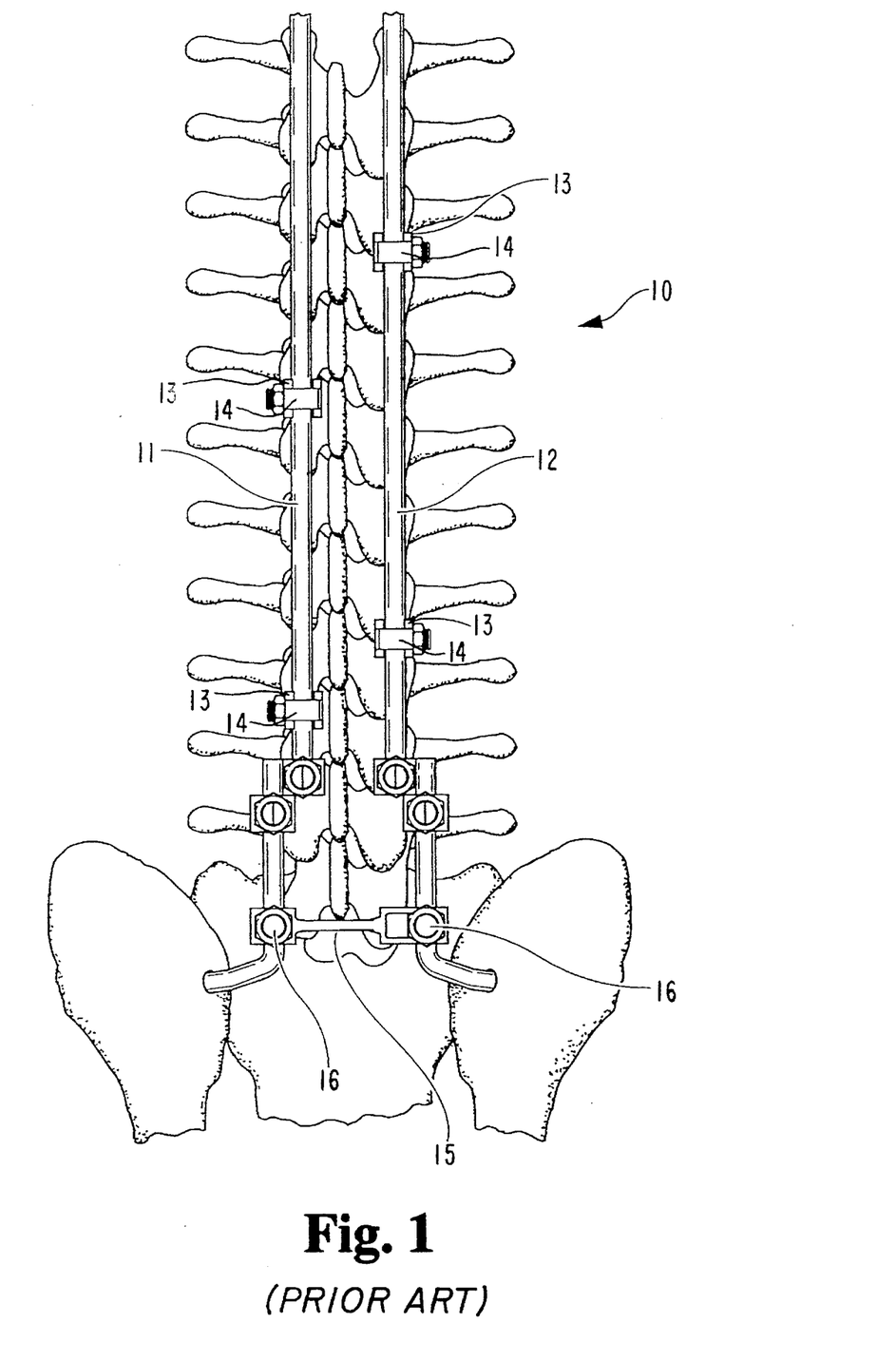
FIG. 1 is a top elevational view of a spinal fixation system of the prior art, namely the TSRH® system of Danek Medical, Inc.

The treatment of spinal deformities and injuries has evolved significantly since the 1970's. Spinal deformities, such as scoliosis and kyphosis, as well as fractures, spondylolisthesis, stenosis, tumors and other medical indications have been treated using a system of relatively rigid rods spanning the vertebral column. One such system for correcting spinal deformities is the TSRH® system provided by Danek Medical, Inc. of Memphis, Tenn. One embodiment of the TSRH® system is shown in FIG. 1. In this TSRH® rod system, a pair of rods 11 and 12 span the length of the spinal column, particularly from the lower lumbar vertebrae to the thoracic vertebrae. A number of fixation hooks 13 are engaged to the rods by eyebolts 14 at various vertebral levels along the construction. These hooks are of well known construction and include a claw for grabbing segments of a specific vertebra. The TSRH® system also provides means for engaging the sacrum for a firm foundation for the rigid construct. A transverse connector 15, provided by Danek as its Cross Link® connector, provides lateral engagement between the parallel rods. In known constructions, a number of transverse connectors 15 can be situated at various locations along the rods as necessary to provide an adequate and stable construct.

The TSRH® spinal system, as well as other systems of this type, permit rigid and semi-rigid segmental instrumentation Of the spine using a selection of hooks, and in some instances bone screws or bolts that engage the pedicle of the vertebra.

In these previous hook and rod spinal systems, correction of spinal deformities is achieved primarily through derotation of the rods. Hooks attached to the rods exert forces at key points of the deformed spine to correct the particular deformity of spinal curvature. In addition, other rod systems provide mechanisms for longitudinal distraction and compression of the hooks as required to account for the particular medical indication. Similarly, the hook and rod systems provide a means for maintaining correct positioning of vertebrae during a vertebral fusion process as may be indicated to correct painful disc syndrome or degenerative disc disease.

While the hook and rod spinal systems of the prior art have provided a very valuable and effective means for correcting spinal deformities or stabilizing spinal injuries, there remains a need for improvement of certain aspects of these spinal systems. For instance, many of the prior systems have a limited ability to obtain correction of spinal deformities by moving the fixation hooks perpendicularly with respect to the rod, that is to pull the spine to a physiologically bent rod where the hooks are already engaged to a portion of a vertebra. Another area open for improvement concerns the ability to add hooks at any point along the spine at any time during a medical procedure to compensate for loss of correction of curvature or inaccurate preoperative planning of hook placement. While A-P and lateral radiographs provide a great deal of information to allow the spinal surgeon to plan hook placement, it is often necessary to modify this plan once the implantation procedure has begun due to unanticipated pathologies of the patient.

A further area of improvement for the hook and rod spinal systems concerns the ease of assembling the system. Consideration in recent times has been given to "top loading" the spinal rods. In this feature, the hooks are engaged to the appropriate vertebrae, the rod is positioned relative to the hooks and the eyebolt or other fastener is tightened, all posteriorly. Nevertheless, there still remains a need for a simpler and more efficient method for assembling this system to eliminate the "fiddle factor" that is present in most known hook and rod spinal systems.

SUMMARY OF THE INVENTION

The present invention contemplates a spinal implant system for correcting spinal deformities and abnormalities that uses an elongated spinal rod configured to be implanted adjacent the spinal column and spanning across several vertebral levels. A number of fixation elements, such as spinal hooks, are provided for engaging vertebrae at a number of vertebral levels. According to the present invention, at least some of the fixation elements includes an elongated stem projecting from the vertebra engaging portion. In one important aspect of the invention, rod connector means are provided for connecting the stem of each fixation element to the spinal rod. The rod connector means includes a connector having a one-piece body defining a rod channel adapted to receive the spinal rod therethrough, a stem bore adapted to receive a stem therethrough, and a threaded bore. A threaded set screw is provided which is adapted to be received within the threaded bore. The stem bore has a length through the body and the rod channel intersects the stem bore along a portion of this length to permit contact between the rod and the stem of a fixation element when the rod is received within the rod channel and the stem is received within the stem bore.

In one embodiment of the invention, the threaded bore intersects the stem bore to permit contact between the set screw and the stem within the stem bore as the set screw is threaded into the threaded bore. As the set screw is threaded further into the threaded bore, it presses the stem against the spinal rod to provide a clamped engagement and to restrain relative movement between the rod and the fixation element. In a further embodiment, the threaded bore intersects the rod channel so that the set screw bears against the spinal rod when the rod is within the rod channel. In this embodiment, as the set screw is threaded further into the threaded bore, it presses the rod against the stem of the fixation element to again provide a clamped engagement between the rod and the stem of the fixation element.

In a further important aspect of the invention, the connector body of the rod connector means further defines a channel opening extending to the rod channel which is sized to permit passage of the spinal rod therethrough when the rod is to be received within the rod channel. This channel opening permits "top-loading" of the rod connector means when the spinal rod is already in position adjacent the spinal column. The stem bore in the connector body has an elongated cross-section with a length along the long axis of the cross-section that is greater than the width of the fixation element stem. This greater length allows the stem to move back within the stem bore to allow the connector body to engage the spinal rod even when the stem is extending through the stem bore. Once the connector body is disposed in its final implanted position, the set screw can be tightened to draw the stem and the spinal rod together into a rigid construct.

In a further feature of the invention, the stem of the fixation elements can include a groove defined along the length of the stem, the groove forming opposite groove tips adapted to firmly grip the spinal rod. The spinal rod can further include a spiral groove formed along its length, with the groove tips of the fixation element stem sized to fit within the spinal rod spiral groove. This feature of the invention adds a greater element of security against the fixation element stem sliding along the length of the spinal rod.

The spinal implant system of the present invention further contemplates a lateral offset coupler which permits adjustment of the lateral position of a fixation element relative to the spinal rod. In one embodiment, the lateral offset coupler includes an offset body with means for engaging a fixation element, and a stem extending from the offset body. The stem is preferably configured identically to the fixation element stem described above so that the same rod connector means can be used to connect the lateral offset coupler to the spinal rod. In one specific embodiment of the lateral offset coupler, the offset body is perpendicularly offset from the stem to permit superior/inferior offset of the fixation element when the lateral offset coupler is connected to the spinal rod.

One feature common to the stem of the fixation elements and the stem of the lateral offset coupler resides in external threads formed along a portion of the length of both seems. The threads are adapted to receive a correspondingly threaded nut which forms part of a means for temporarily fastening the components to the rod connector means. Specifically, in the case of the threaded stem of the fixation elements, the stem is long enough to extend significantly above the level of the spinal rod when the rod is initially positioned near the spinal column. When the rod and stem are situated within the rod connector body, the nut can be threaded onto the threads of the fixation element stem. As the nut is tightened down onto the stem threads, it bears against the connector body, pushing the body, and the spinal rod with it, closer to the vertebra engaging portion of the fixation element. In other words, the present invention provides for a method of implanting a spinal system in which the bulk of the instrumentation procedure can be accomplished at a level dorsal to the instrumented vertebrae, allowing easier unencumbered assembly. When the orientation of the construct and arrangement of vertebral fixation elements meets with the surgeon's satisfaction, the construct can be drawn anteriorly down to its final implant level adjacent the vertebrae by threading each of the nuts down on the threaded stems of the fixation elements. Once the spinal rod has reached its final location, the set screws in each of the rod connector means can be tightened to firmly clamp rod to fixation element, thereby completing the implant construct. The same components can be used as a reduction apparatus to draw a misplaced vertebra into alignment with adjacent properly positioned vertebrae.

It is therefore one object of the invention to provide a spinal implant system that dispenses with the "fiddle factor" associated with prior systems in which the fixation components must be pre-loaded onto the spinal rod. A further object resides in features of the present inventive system that provide top-loading of rod connectors that can be used in a variety of orientations to connect fixation elements, transverse connectors and lateral couplers alike.

A benefit attained by the present invention is the ability to initially instrument the spine at a higher posterior level and then subsequently draw the construct-down to its final position adjacent the vertebrae. A further object resides in providing a system that allows the surgeon to add vertebral fixation elements or change the position or level of instrumentation while the spinal rod is oriented along the spinal column.

Yet another object of the invention is to provide an implant system having a reduced profile from prior rod systems. Other objects and benefits of the present invention will become apparent upon consideration of the following written description taken in conjunction with the accompanying figures.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
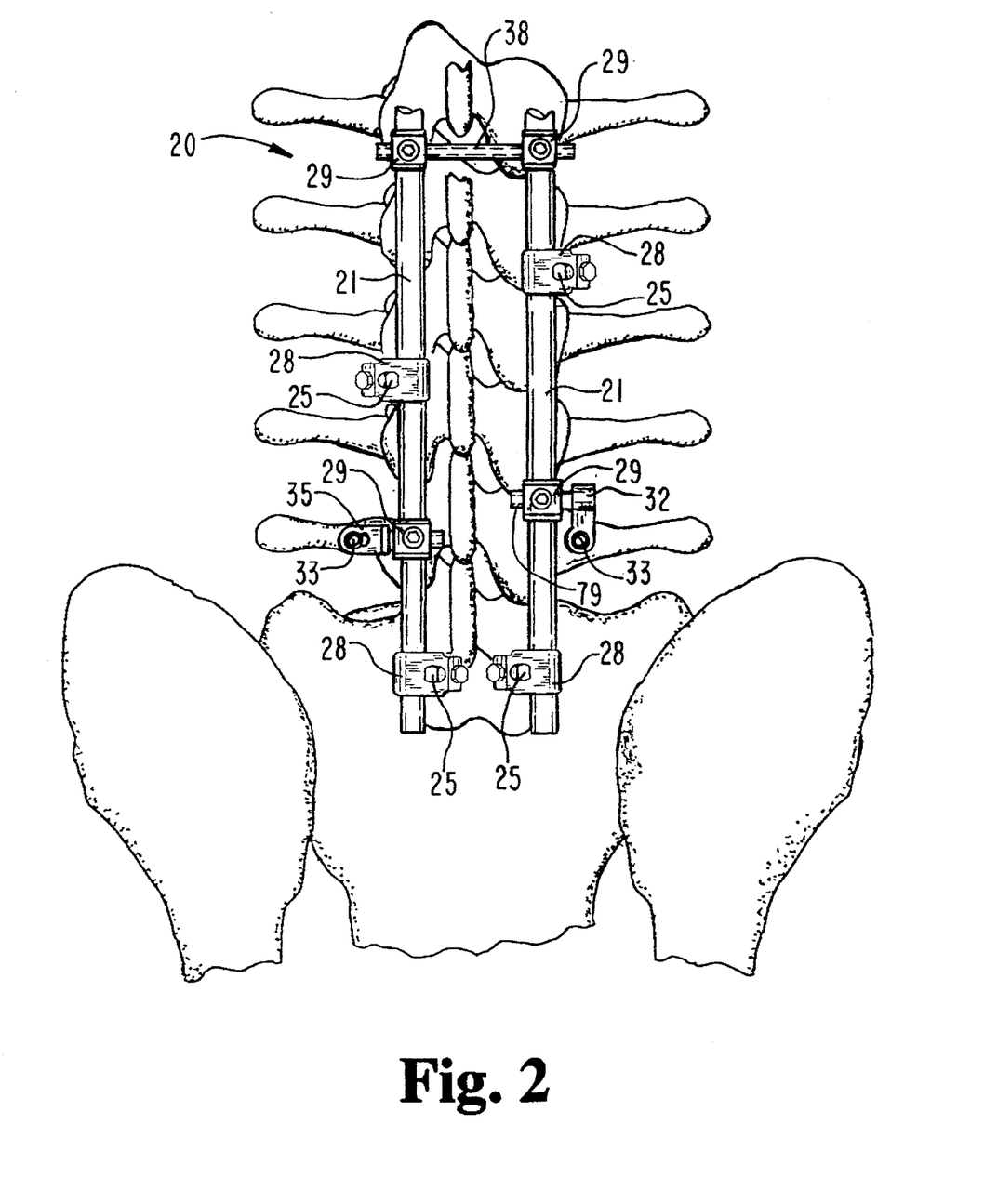
FIG. 2 is a partial top elevational view of a spinal fixation system in accordance with the present invention showing various components of the system for engaging the vertebrae.

Referring now to FIG. 2, a spinal fixation system 20 in accordance with the present invention is illustrated. The system includes a pair of bendable elongated spinal rods 21 situated on opposite sides of the spinal column and particularly the sagittal plane. The rods 21 as depicted in FIG. 2 are shown extending from the sacrum to the upper lumbar vertebrae. It is understood, of course, that the rods can extend to the thoracic vertebrae or between any group of vertebrae in the spinal column as indicated to correct the particular spinal deformity or treat the specific spinal problem.

In the-construct of the spinal fixation system 20, a number of fixation hooks 25 are engaged to the rod 21 at various locations along the vertebral column. As in prior spinal fixation systems, such as the TSRI® system described above, these fixation hooks engage predetermined segments of the spinal column to provide the appropriate forces for fixation or correction of spinal deformities. Each of the fixation hooks 25 is engaged to a respective rod 21 by way of a rod connector means 28. Other rod connectors means 29 are used to mount other components to the spinal rods 21, such as an offset coupler 32. The offset coupler 32 provides a means for supporting a bone screw 33 offset from the fixation position on the rod in the lateral and superior/inferior directions. The rod connector means 29 are also used to support a transverse coupler 35 which also engages a fixation screw 33 at variable lateral distances. A transverse connector 38 can be provided to add lateral stability and fixation between the two rods 21.

Figure 3A:
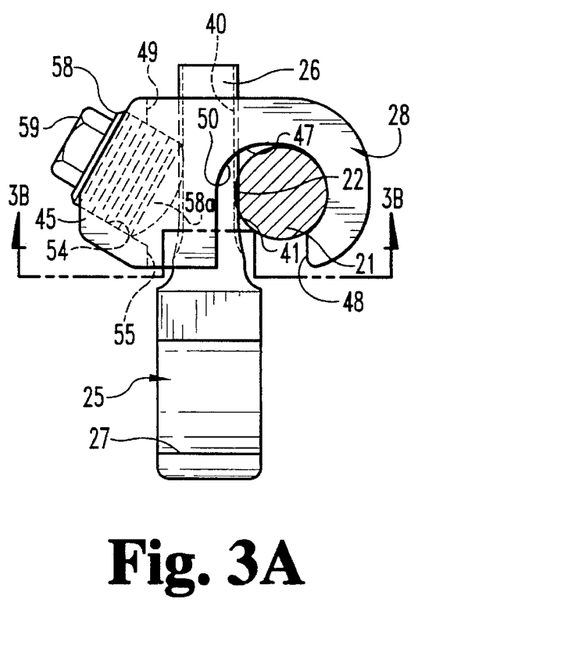
FIG. 3A is a side view of a rod connector and hook an arrangement implemented according to the present invention with a spinal hook clamped to longitudinal fixation rod.
Figure 3B:
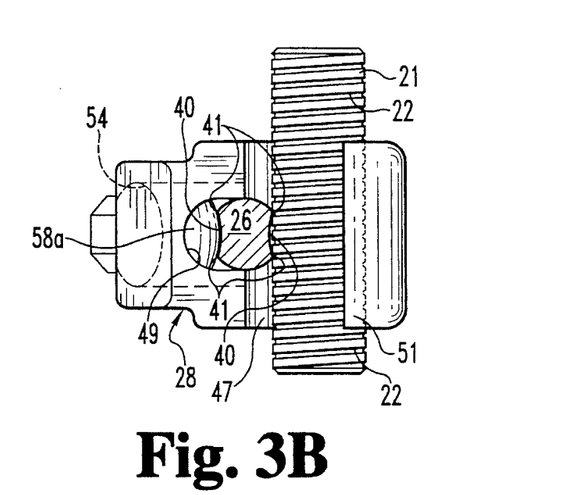
FIG. 3B is a bottom partial cross-sectional view of the rod connector and hook system shown in FIG. 3A taken along line 3D-3B as viewed in the direction of the arrows.
Figure 3C:
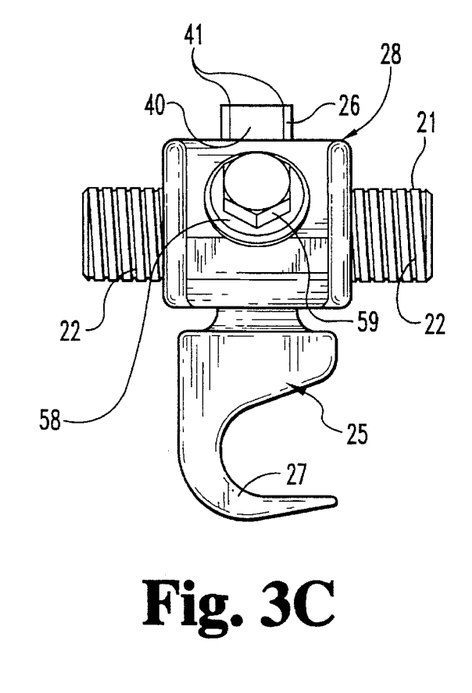
FIG. 3C is a further side view of the rod connector and hook assembly as viewed rotated 90° from the appearance in FIG. 3A.

With this general description of the construct of the spinal fixation system 20 of the present invention, attention now can be turned to the specific components of the system. One embodiment of the rod connector means 28 is shown in FIGS. 3A–3C. It can be seen that the rod connector means 28 provide a means for engaging a fixation element, such as hook 25, to the spinal rod 21. The fixation hooks 25 includes an elongated stem 26 and an integral claw portion 27 which engages a portion of a vertebra. The rod connector means 28 includes a connector body 45 which defines a rod channel 47 through which the spinal rod 21 extends. In one specific embodiment, the rod channel 47 includes a channel opening 48 so that the rod connector means 28 can be "top-loaded" onto the spinal rod 21. Alternatively, the channel opening 48 can be eliminated so that the rod channel 47 is in effect a bore through the connector body 45. In this instance, with the "closed" rod channel configuration, the rod connector means 28 must be preloaded onto the spinal rod prior to placement of the rod in the patient. In this manner, the closed channel rod connector means would operate similar to the eyebolt fixation component of the TSRH® system previously described. The open channel configuration is preferred to retain the flexibility afforded by the top-loading capability. Top-loading means that a surgeon can acid new fixation elements and rod connector means as necessary at virtually any stage of the spinal instrumentation procedure, even with the spinal rod in position adjacent the spine.

The connector body 45 of the rod connector means 28 further defines a stem bore 49 which is oriented perpendicular to the rod channel 47 and which intersects the rod channel at an overlap portion 50. The stem bore is adapted to receive the fixation element stem 26 therethrough and, as can be seen more particularly in FIG. 3B, can be in the shape of an elongated slot that is larger than the general width of stem 26. However, it is an essential feature of the rod connector means 28 of the present embodiment that the bore 49 include the bore/channel overlap 50 to permit the stem 26 of the fixation hook 25 to contact the rod 21 when the rod is situated within the rod channel 47.

The body of the rod channel 47 defines-a rod/channel overlap portion 51, as shown in FIG. 3B, which serves to retain the rod 21 within the channel 47. The pressure-between the stem 26 of the hook 25 and the rod/channel overlap portion 51 of the connector body 45, clamps the rod to the rod connector means 28. This pressure is provided by way of a set screw 58 which is threaded into a set screw bore 54. As can be seen in FIG. 3A, the set screw bore is oriented fat an angle to both the stem bore 49 and the rod channel 47 and intersects the stem bore 49 at an intersection 55. In this manner, a set screw 58 threaded into the bore 54 can contact and apply pressure to the hook stem 26. As the set screw 58 is threaded deeper into the set screw bore 54, the curved tip 58a of the screw applies pressure to the stem and clamps the stem 26 and the rod 21 between the connector body 45 and the set screw 58.

In this specific embodiment, the set screw 58 includes a driving head 59 which can be of a typical bex configuration. When the driving head 59 is a hex head extending beyond the surface of the connector body 45, the angular orientation of the set screw bore 54 helps to reduce the posterior profile of the rod connector means 28. In addition, it has been found that this particular angular orientation of the set screw 58 often facilitates tightening the set screw within the bore 54. It is of course understood that the driving head 59 can be replaced by a hex recess for engagement to an allen head tool.

The rod 21 of one specific embodiment includes a feature for preventing the rod connector means 28 from shifting along the length of the rod 21. In particular, the rod 21 includes a spiral groove 22 formed in the outer surface of the rod, as shown in FIGS. 3B and 3C. In addition, the stem 26 of the fixation hook 25 can include a pair of shallow grooves 40 on opposite faces of the stem. The grooves form tips 41 at the edges of the grooves, which tips engage within the spiral groove 22 of the rod 21. It has been found that the interface between the groove tips 41 and the rod spiral groove 22 adds a greater degree of longitudinal stability to the rod connector means 28 to prevent the connector from sliding along the rod during or after instrumentation. The groove 40 in the hook stem 26 provides a contoured surface for receiving the oval point 58a of the set screw 58. This allows for maximum frictional contact between the set screw 58 and the hook stem 26, thereby reducing the likelihood of slippage in the posterior/anterior direction of the hook relative to the connector 28. It has been found that the groove tips 41 can deform slightly when pressed against the spinal rod 21, with or without the spiral groove 22, to provide an additional frictional fit.

Figure 4:
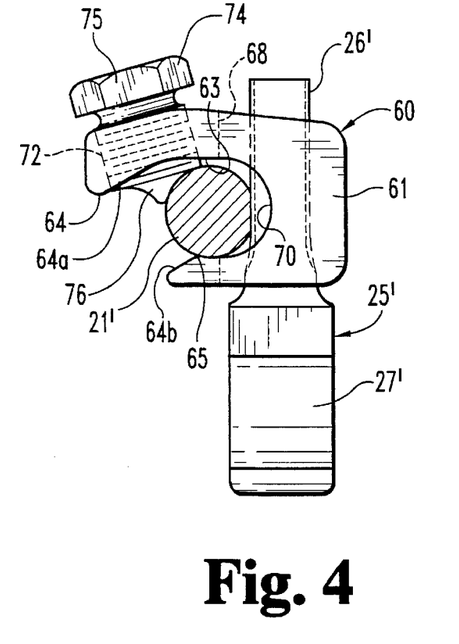
FIG. 4 is a side partial cross-sectional view of a rod connector and hook assembly in an alternative embodiment of the present invention.

An alternative embodiment of the rod connector is shown in FIG. 4. In this embodiment, the rod connector means 60 includes a connector body 61 which defines a rod channel 63. The body further defines a channel opening 64 which opens generally laterally relative to the body 61. The body 61 also defines a stem bore 68 through which the stem 26' of a fixation hook 25' can extend. The channel opening 64 of the rod channel 63 is oriented at a somewhat anterior angle to the stem bore 68. On the other hand, in the rod connector means 28 of the previous embodiment shown in FIG. 3A, the channel opening 48 extends generally parallel to the stem bore 49.

The channel opening 64 of the connector body 61 is defined by a pair of parallel faces 64a and 64b. These parallel faces 64a and 64b provide a surface along which the connector 60 slides along the rod 21' when the connector is to be engaged to the rod. While the rod connector means 60 is intended to be a top-loaded component, similar to the rod connector means 28, the engagement of the connector 60 to the spinal rod 21 requires some degree of lateral manipulation to snap the rod through the channel opening 64 into the rod channel 63. The lower parallel face 64b includes a locking edge 65 at the channel opening 64 which helps retain the rod 21' within the rod channel 63.

The stem bore 68 defines a bore/channel overlap 70, similar to that found in the rod connector means 28 of the previous embodiment. Thus, when the stem 26' of a fixation hook 25' extends through the stem bore 68, the stem 26' can contact the rod 21'. This contact is maintained by way of a set screw 74 which is threaded into a set screw bore 72 at the upper arm of the channel 64, and particularly through the upper parallel face 64a. The set screw 74 includes a driving head 75 and a rod engaging taper 76 at the opposite end of this set screw. This taper 76 is generally conical in shape and has a curvature which approximates the curvature of the spinal rod 21'. In this specific embodiment, it can be seen that the rod 21' does not include the spiral groove 22 described above. Moreover, the stem 26' of the hook 25' does not include the grooves 40 in the opposite faces of the stem. It has been found that with this configuration of rod connector means 60, the three points of contact to the rod 21' essentially eliminate the need for the spiral groove 22 and stem groove 40. As can be seen from FIG. 4, the rod 21' is clamped between the rod channel 63, particularly at the locking edge 65, the hook stem 26', and the tapered tip 76 of the set screw 74. On the other hand, as can be seen by comparison to FIG. 3A, the rod 21 is engaged only between the rod channel 47 and the grooved stem 26 of the hook 25. The manner in which the two rod connector means 28 and 60 snap on to the spinal rod 21 or 21' may dictate which of the particular connectors is used at a specific level of instrumentation. It has been found that either of the two connectors 28 or 60 provide a solid engagement of the fixation hook 25 or 25' to the longitudinal spinal rod.

Both of the rod connector means 28 and 60 permit top-loading of the connector to connect the fixation element stems to the spinal rod. The channel openings (48 and 64) allow the spinal rod to be slipped into the respective rod channels 47 and 63. The corresponding stem bores 49 and 68 have an elongated cross-section in which the long axis of the cross-section is greater than the general width of the fixation element stem 26. Thus, the stem is allowed to slide to one end of the bores 49/68 providing clearance for the spinal rod to pass into the rod channels. In the case of the rod connector means 28, this clearance is of greater importance to allow the rod to clear the rod/channel overlap 51. On the other hand, the rod connector means 60 eliminates some of this manipulation since the stem bore 68 is at the opposite end of the rod channel 63 from the channel opening 64.

Figures 5, 6, 7, 8A, 8B, 9:
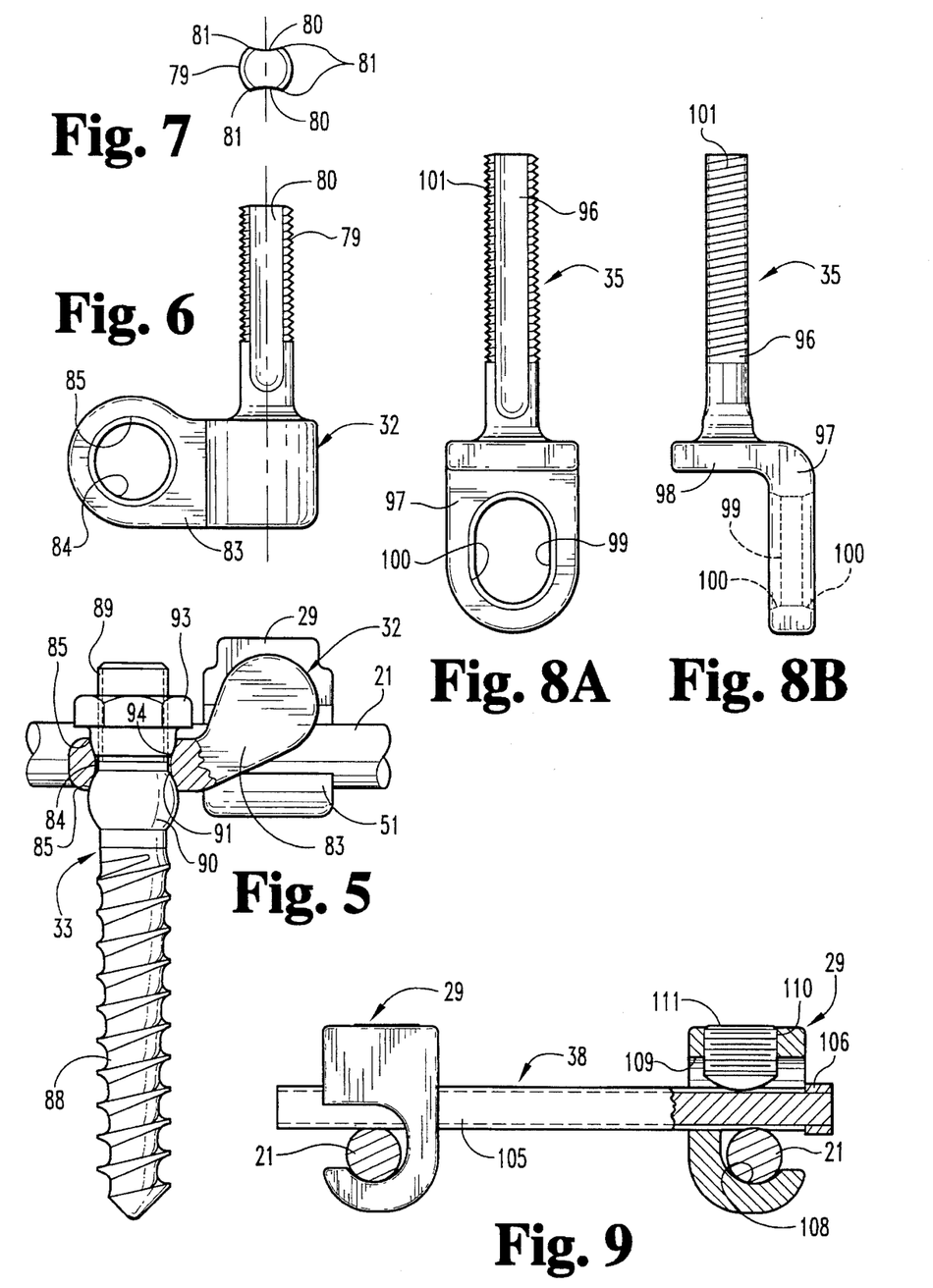
FIG. 5 is a partial cutaway view of an offset coupler in accordance with the present invention.
FIG. 6 is a top elevational view of the offset coupler component shown in FIG. 5.
FIG. 7 is an end view of the stem of the offset coupler shown in FIG. 6.
FIG. 8A is a top elevational view of a transverse coupler in accordance with the present invention.
FIG. 8B is a side elevational view of the transverse coupler shown in FIG. 8A.
FIG. 9 is an end partial cross-sectional view of the transverse connector assembly in accordance with the spinal fixation system of the present invention.

Referring now to FIGS. 5–7, a further component of the spinal fixation system 20 of the present invention is shown. In particular, the offset coupler 32 previously illustrated in FIG. 2, provides a means for engaging a bone fastener 33 (either a screw or bolt) to the spinal rod 21. The offset coupler 32 includes a stem 79 (FIG. 6) which includes upper and lower grooves 80. The grooves define groove tips 81, as shown in FIG. 7. The offset coupler 32 further includes an offset body 83 which is oriented generally perpendicular to the stem 79. In addition, as shown in FIG. 5, the offset body 83 angles downward somewhat from the longitudinal axis of the stem 79 so that the screw bore 84 in the body 83 is at or below the level of the spinal rod 21. The bore 84 through the body 83 also includes upper and lower countersunk portions 85.

As shown in FIGS. 2 and 5, the stem 79 of the offset coupler 32 can be engaged to the spinal rod 21 by way of a rod connector 29. In one specific embodiment, the rod connector 29 can be the rod connector 28 or the rod connector 60. However, as should be apparent from FIG. 5, the rod/channel overlap 51 of the rod channel 47 is oriented at the underside, or anterior side, of the spinal rod 21, as opposed to the lateral engagement shown in FIG. 3A. This orientation of the rod connector 28/29 allows the stem 79 of the offset coupler 32 to contact the spinal rod 21 at the posterior, or top, side of the rod.

The offset coupler 32 provides a means for engaging a bone fastener 33, such as a screw or bolt to the rod 21. The details of the threaded fastener 33 is shown in FIG. 5. In particular, the fastener 33 includes bone engaging threads 88 which are adapted to be threaded into the pedicle of a vertebra such as a lumbar vertebra. At the opposite end of the fastener 33 are machine threads 89 which are adapted to engage a threaded nut 93. Between the machine threads 89 and the bone threads 88 is an intermediate portion 90. This intermediate portion 90 includes an upper arcuate surface 91 which is seated against the underside countersink 85 of the screw bore 84 in the offset body 83. Similarly, the nut 93 includes an arcuate seat 94 which engages the upper countersink 85 in the offset body 83.

It has been found with this specific embodiment of the threaded fastener 33 that the engagement between the countersinks 85 and the arcuate surfaces of the intermediate portion 90 and the nut 93 allows for some degree of angulation of the fastener 33 relative to the offset coupler 32. In practice it can be difficult to perfectly align the offset coupler 32 with the particular vertebral segment to be instrumented. Thus, the ability to orient the threaded fastener 33 relative to the rod 21 enhances the ability of the surgeon to instrument the spine. Of course, it is understood that in certain applications the threaded fastener 33 need not include the arcuate surface 91 and can simply include a flat engagement surface, such as found in bone bolts having an integral hex driving nut feature. When the threaded fastener 33 is a bone bolt, it is anticipated that the bolt would be first threaded into the particular vertebra at the level of instrumentation. The offset coupler 32 is then be engaged to the bolt and subsequently fastened to the spinal rod 21 by way of a rod connector 29. Alternatively, the offset coupler 32 may already be engaged to the rod 21 by a connector 29, after which the coupler 32 and threaded fastener 33 are pulled together and engaged. The threaded fastener 33 may be a bone screw which does not include an intermediate portion 90 that engages the underside of the offset body 83. In this instance, it can be expected that the offset body 83 is configured to project a little further below the spinal rod 21 to contact the surface of the vertebra when the screw is threaded into the bone.

A transverse coupler 35 in accordance with the present invention is shown in FIGS. 8A and 8B. The transverse coupler 35 provides for lateral offset engagement of a threaded fastener 33 between the bone and spinal rod 21. The transverse coupler 35 is similar to the offset coupler 32 except that it does not include an anterior/posterior offset feature. Specifically, the transverse coupler 35 includes a stem 96, which can be a grooved stem such as the stem 79 of the offset coupler 32. Integral with the stem 96 is an offset body 97, which includes an anterior offset portion 98 to bring the body 97 closer to the vertebra when the transverse coupler 35 is engaged to the spinal rod 21. The offset body 97 includes a screw slot 99 having upper and lower countersinks 100. The slot 99 can simply be a circular bore or can be somewhat elongated to allow for further variation in lateral position of the threaded fastener 33 relative to the transverse coupler 35. In the case of both the offset coupler 32 and the transverse coupler 35, it is anticipated that the respective stems 79 and 96 are long enough to allow for some lateral or transverse variation in position. In addition, the stems 79 and 96 can include threads along their length, such as threads 101 shown in FIG. 8B. These threads 101 are adapted to receive a nut which is threaded onto the stem when the stem is loosely disposed within a rod connector 29 in position on the spinal rod 21. The threads 101 and the additional temporary nut can be used to draw the transverse coupler 35, and particularly the threaded fastener 33 supported by the coupler, toward the spinal rod 21. That is, as the nut is threaded onto the threads 101, the rod 21 and the threaded fastener 33 are pulled together. Once the appropriate orientation of rod to fastener is achieved the rod connector 29 and particularly the set screw of the rod connector, can be tightened to clamp the stem 96 to the rod 21. Once the rod connector 29 has clamped the transverse coupler 35 to the rod 21, the temporary nut can be removed and the excess portion of the stem extending beyond the rod connector can be sheared off and removed.

The spinal fixation system 20 of the present invention further contemplates the use of a transverse connector 38 to provide transverse or lateral interconnection between the two spinal rods 21. As shown in FIG. 9, the transverse connector 38 includes a stem 105 terminating at one end in a head portion 106. The stem of the transverse connector is configured to pass through stem bores of rod connectors 29 engaged to each of the two rods 21. As discussed above, the rod connectors 29 can be configured as either the rod connector 28 or 60. Alternatively, the rod connectors 29 can be configured as shown in FIG. 9 to include a rod channel 108 and a posteriorly oriented set screw bore 110. The stem bore 109 projects perpendicularly to the set screw bore 110, but parallel to the opening of the rod channel 108. The set screw 111 can include a hex head recess to receive an allen head tool. In this manner, the rod connector 29 is readily adapted for receiving a driving tool directly posterior to the rod and transverse connector 38. The set screw 111, which is preferably similar to the set screw 58, which includes an oval point for engaging the stem 105 of the transverse connector 38. Again, as with the transverse coupler 35, the stem 105 of the transverse connector 38 can be threaded to allow a temporary nut to be tightened onto the stem. As the temporary nut is tightened onto the stem, the spinal rods 21 engaged by the rod connectors 29 are drawn together. The head 106 at the one end of the transverse connector 38 provides an additional reaction surface in combination with the temporary nut. Once the appropriate position between the two rods 21 has been achieved, the rod connectors 29 can be tightened to firmly engage the stem 105 of the transverse connector 38 to each of the rods, and the temporary nut removed.

Figures 10A, 10B, 10C:
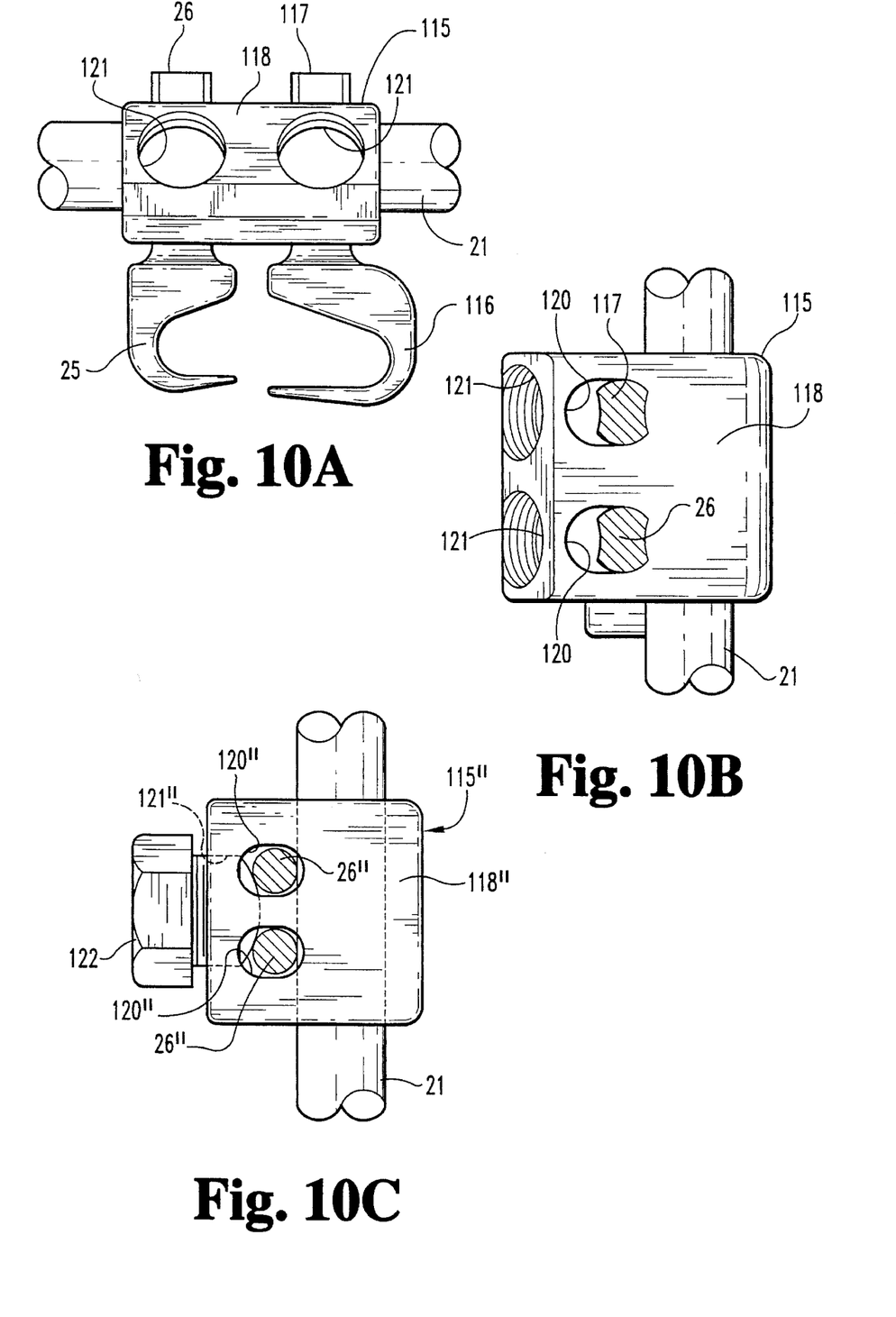
FIG. 10A is a side elevational view of a dual hook connector assembly in accordance with the present invention.
FIG. 10B is a top elevational view of the dual hook connector shown in FIG. 10A.
FIG. 10C is a top elevational view of a dual hook connector shown in FIG. 10B modified to utilize a single set screw.

Referring now to FIGS. 10A and 10B, a dual hook connector 115 is shown which provides means for engaging a pair of hooks to a spinal rod by way of a single connector. The dual hook connector 115 includes a connector body 118 which receives the stems 24 of a pair of hooks. Specifically, the hooks can be a hook such as hook 25 having a stem 26, as well as a differently configured laminar hook 116 having a stem 117. The two hooks can have their claws facing each other to engage the lamina of a vertebra therebetween. Each of the stems 26 and 117 extend through a respective stem bore 120 defined in the body 118. A pair of set screw bores 121 intersect the stem bores 120 so that a pair of set screws (not shown) can be threaded therein to clamp the stems to the spinal rod. The distance between the stem bores 120 and set screw bores 121 are established to permit sufficient space between the claws of the respective hooks 25 and 116 to engage the lamina at a particular vertebral level. It is understood that the dual hook connector 115 can be configured in the style of the open connectors 28 or 60 described above. In other words, the invention contemplates a dual hook connector in which two open connectors, such as connector 28, are integrally disposed side-by-side to support two spinal hooks.

In a modification to the dual hook connector, a connector 115" shown in FIG. 10C is configured to utilize a single set screw 122 to clamp the stems 26" of laminar hooks to a spinal rod 21. The connector 115" includes a body 118" having a pair of parallel oblong stem bores 120" formed therein. Intersecting each of the stem bores 120" is a set screw bore 121". The set screw 122, when threaded into the bore 121" contacts both hook stems 26" to clamp them against the rod 21. The stems 26" can be circular in cross section, as shown in FIG. 10C, or can have a cross section as shown in FIG. 10B.

Figure 11:
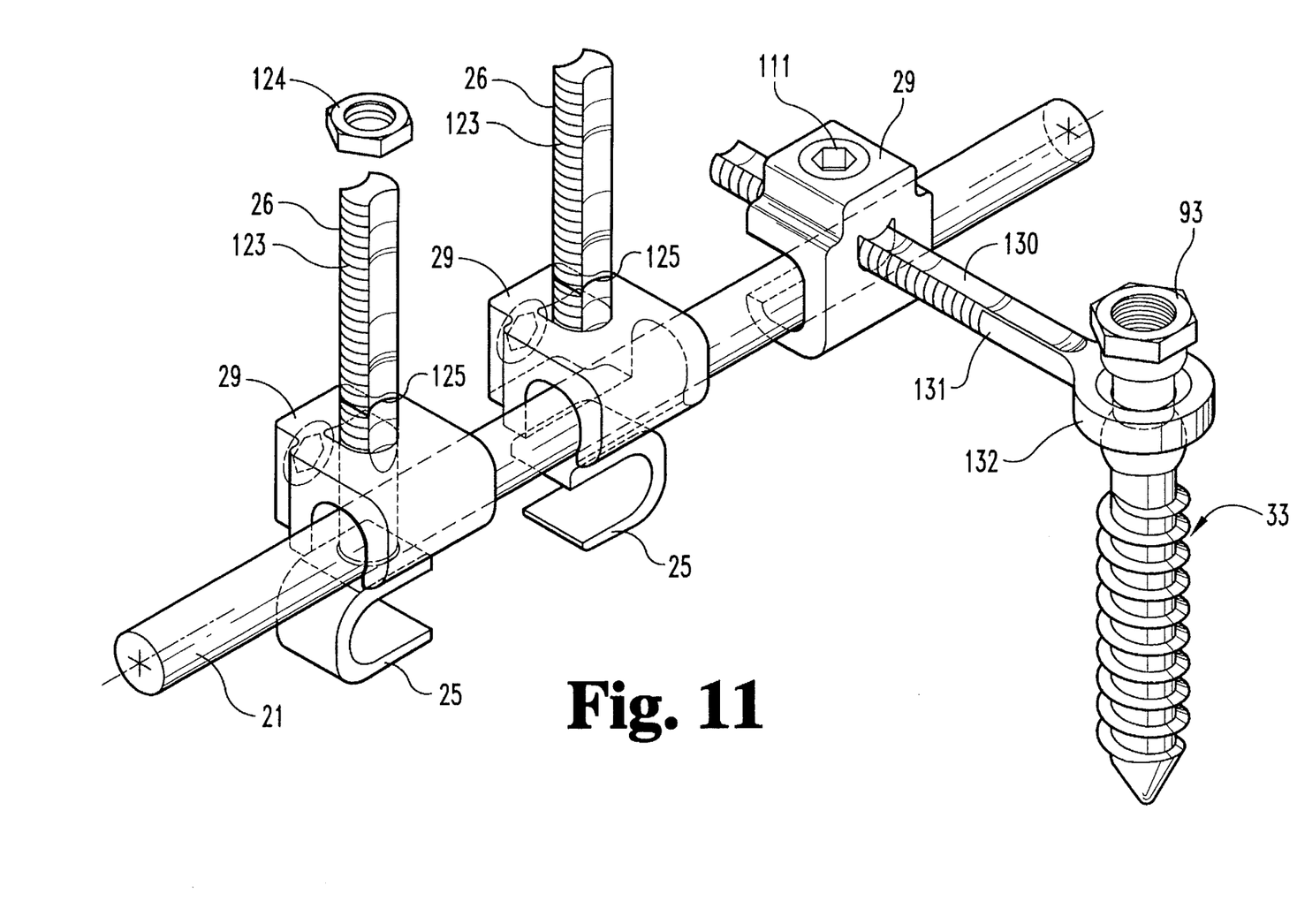
FIG. 11 is a pictorial representation of the spinal fixation system in accordance with one embodiment illustrating one aspect of the method for implanting the system into a patient.

A further transverse coupler 130 is illustrated in FIG. 11. This transverse coupler 130 includes a stem 131 and offset body 132 at one end of the stem. The offset body 132 is configured to support a threaded fastener 33 which is engaged to the body 132 by way of nut 93. As is apparent from this figure, the offset body 132 is at the same level as the stem 131 and does not include any posterior/anterior or superior/inferior offset. This transverse coupler 130, and particularly its stem 131, can be configured similar to the stem 96 of the coupler 35 to include a channel and outer threads.

Certain features of the method of instrumenting the spine using the system 20 of the present invention can be understood with reference to FIG. 11. In this figure, a spinal rod 21" is shown instrumented with a pair of hooks 25" and a threaded fastener 33. The stems 26" of the hooks 25" are engaged to the rod 21" by way of a rod connector 29. In this specific embodiment, the rod connector is the connector 29 having a hex recess set screw 111. Alternatively, the rod connector can be either of the rod connectors 28 or 60 previously described.

As can be seen in FIG. 11, the stems 26 of the hooks 25 are long enough to project significantly outward from the rod 21. These stems are shown in their configuration immediately after having been installed in the spine. The stems, which are preferably about two inches long, allow more ready top-loading of the rod when the hooks are already engaged at the particular vertebral level. In prior systems, the vertebral hooks have a relatively short stem for engagement by the rod instrumentation. This adds to the "fiddle factor" in completing the instrumentation. On the other hand, the present invention contemplates a much longer stem to the hooks, which stem can be severed at a break line 125 once the hooks have been fastened to the spinal rod 21. In accordance with the present invention, the hooks are engaged at the vertebra with the stems extending posteriorly. The rod and rod connector 29 can then be top-loaded onto the stem with the hook stem extending through the bores in the connectors 29. A temporary nut 124 can be threaded onto the threads 123 of each of the hook stems 26 to draw the rod 21 and the instrumented vertebra together. Once the appropriate relationship between rod and vertebra has been achieved, the set screw 111 of the rod connector 29 can be tightened to clamp the stem 26 to the rod 21. At this point, the temporary nut 124 is removed and the stem shortened by severing at the break point 125.

Figure 12:
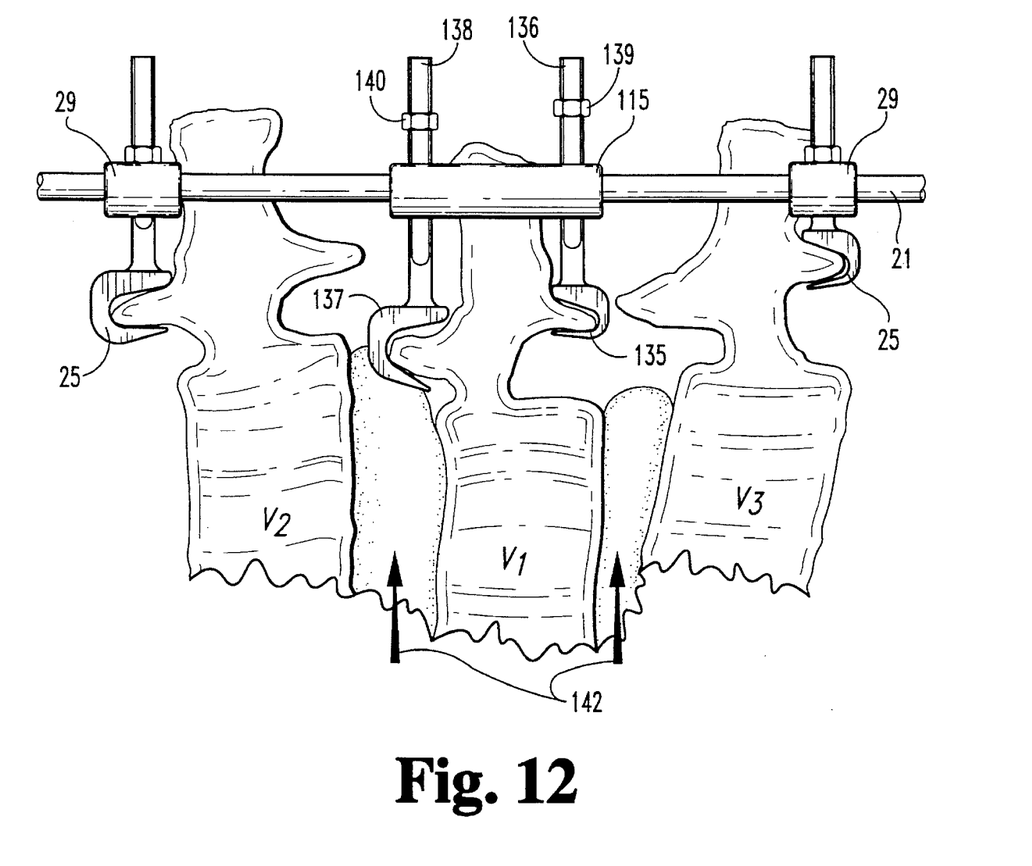
FIG. 12 is a lateral pictorial representation of a portion of the spinal column instrumented with the spinal fixation system in one aspect of the present invention.

The spinal fixation system of the present invention can also be used as a reduction apparatus. As shown in FIG. 12, a displaced vertebra $V_1$ is instrumented between two normally positioned vertebrae $V_2$ and $V_3$. The spinal rod 21 is bent to approximate the spinal physiology of the subject vertebra. The normal vertebra $V_1$ and $V_3$ are engaged by the claws of spinal hooks 25. The hooks 25 are attached to the spinal rod 21 by way of rod connectors, such as rod connectors 29 described above. The displaced vertebra $V_1$ is instrumented with laminar hooks 135 and 137. Each of the hooks 135 and 137 has a corresponding elongated stem 136 and 138, respectively. The stems extend through a dual hook connector, such as connector 115 described with respect to FIGS. 10A and 10B. A pair of nuts 139 and 140 are threaded onto stems 136 and 138, respectively. As the nuts are tightened down onto their corresponding stems, the hooks 135 and 137 draw the displaced vertebra $V_1$ toward the spinal rod 21, in the direction of the arrows 142. The nuts 139 and 140 are continually tightened onto the stems 136 and 138 until the vertebra $V_1$ is in proper alignment relative to the other instrumented vertebrae $V_2$ and $V_3$.

Thus can be seen that the spinal fixation system according to the present invention includes multi-level instrumentation capabilities which can be used for two purposes. The first purpose is to permit instrumentation at a higher level above the vertebrae and then be drawn down to a level immediately adjacent the vertebrae. The second use is as a reduction apparatus to draw a displaced vertebra into proper physiological alignment.

Alternative embodiments of certain components of the spinal fixation system of the present invention are also contemplated. For instance, referring now to FIGS. 13A and 13B, a closed rod connector 145 is shown. The rod connector 145 includes a body 146 which defines a rod channel 147 therethrough. The rod channel 147 is generally oblong in shape and is defined by a pair of overlapping bores 148 and 149. The bore 148 has approximately the same diameter as the spinal rod 155; while the bore 149 portion of the rod channel 147 has a somewhat larger diameter. The rod connector 145 is a closed connector in the sense that the rod channel 147 does not include a channel opening through the sidewall of the body 146. Thus, the connector 145 must be pre-loaded onto the spinal rod 155 prior to instrumentation of the vertebra. Initially during instrumentation, the rod 155 will nominally reside within the diameter 148 of the channel 147.

Figure 13A:
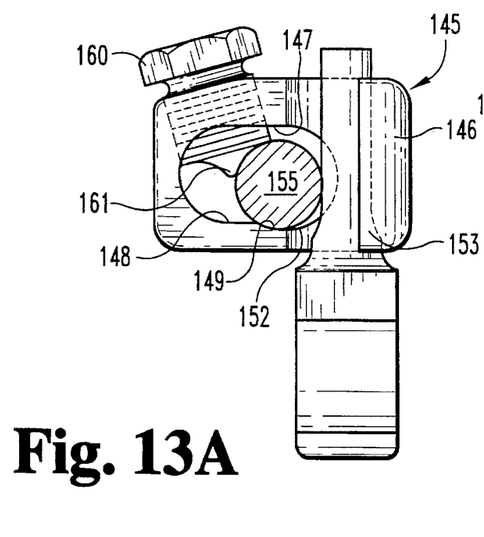
FIG. 13A is a side view of a rod connector in accordance with another embodiment of the present invention.
Figure 13B:
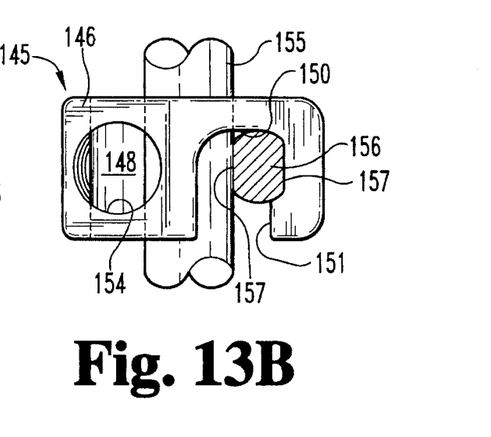
FIG. 13B is a top view of the rod connector shown in FIG. 13A.

The rod connector 145 further includes a stem channel 150 which includes a channel opening 151 through the sidewall of body 146. The channel opening 151 allows the rod connector 145 to readily engage the stem 156 of a spinal hook already engaged to a vertebra. The elongated rod channel 147 allows the spinal rod 155 to be situated away from the stem channel 150 until the stem 156 is moved through the channel opening 151.

The rod channel 147 and the stem channel 150 overlap at a portion 152. This overlap 152 allows the spinal rod 155 to be pushed into direct contact with the stem 156. The stem channel 150 also includes an overlap 153 which holds the stem 156 in place. It can be seen that the stem 156 includes opposite flat surfaces 157 to provide a greater contact surface between the stem 156, and the stem channel 150 and spinal rod 155.

The body 146 of the rod connector 145 further defines a set screw bore 154 which intersects the rod channel 147. A set screw 160 is then threaded into the bore 154 so that the tip 161 contacts the spinal rod 155 and urges it into frictional engagement with the stem 156.

Figures 14, 15, 16:
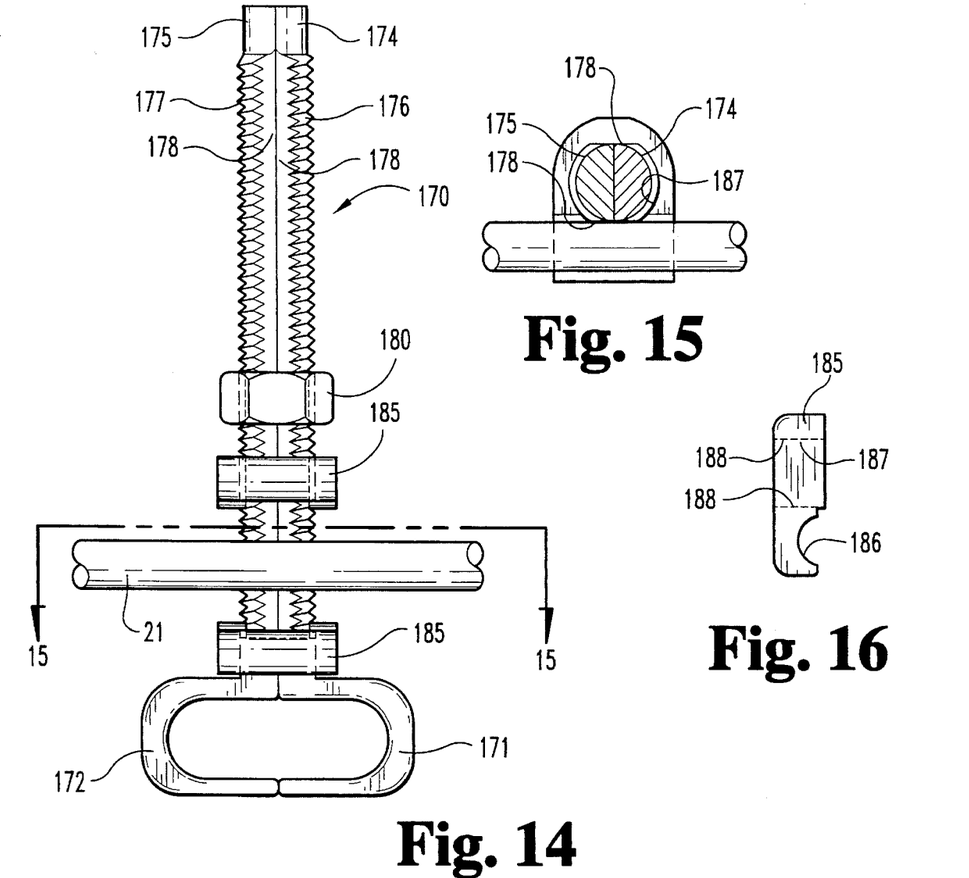
FIG. 14 is a side view of a facing hook assembly in accordance with one aspect of the present invention.
FIG. 15 is a top cross-sectional view of the facing hook assembly shown in FIG. 14, taken along line 15—15 as viewed in the direction of the arrows.
FIG. 16 is a side view of a clamp half used in connection with the facing hook assembly shown in FIG. 14.

In a further aspect of the invention, a dual facing hook assembly 170, shown in FIGS. 14–16, is provided which includes a pair of hooks 171 and 172 which can be instrumented on a vertebra in a facing orientation. The hooks 171 and 172 include respective stems 174 and 175. In a novel feature of this assembly 170, each of the stems 174 and 175 includes partial threads 176 and 177 respectively. These threads are formed so that when the two stems 174 and 175 are adjacent one another, as shown in FIG. 15, a fully threaded cylindrical rod is formed. A nut 180 can then be threaded onto the combined stems 174 and 175 to clamp the stems together and to provide a means for engaging a spinal rod 21.

The assembly 170 further includes a pair of clamp halves 185 which are designed to trap a spinal rod 21 therebetween in clamped engagement. Each clamp half 185 defines half of a bore 186 so that when the two halves are combined they form a bore for receiving the rod 21 therethrough. In addition, each clamp half defines a second half bore 187 which is configured to receive the two stems 174 and 175 when the two clamp halves are combined. In one feature of this embodiment, the clamp halves 185 and the stems 174 and 175 are configured for keyed engagement. Specifically, the stems include flat opposite surfaces 178 which correspond to similarly configured flat surfaces 188 of the second half bore 187 in each clamp half 185. This keyed arrangement provides for a specific orientation of the clamp halves 187 relative to the stems 174 and 175 so that the spinal rod 21 is oriented parallel to the opening of the spinal hooks 171 and 172.

It can be seen that the present invention provides a much easier method for assembly in which the construct is formulated at a higher level and then ultimately brought anteriorly down to a lower profile level immediately adjacent the spine. This facilitates the addition of other hooks and connectors if and when it is determined that the proposed instrumentation plan requires modification. With the spinal rods initially oriented at a higher dorsal or posterior level above the vertebrae, the addition of components is more easily achieved.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected:

What is claimed:

1. A spinal implant system for correcting spinal deformities and abnormalities, comprising:

an elongated spinal rod configured to be implanted adjacent the spinal column of a patient spanning across several vertebral levels;

a fixation element for engaging a vertebra;

a lateral offset coupler having an elongated coupler stem and an integral offset body, said offset body including means for engaging said fixation element; and rod connector means for connecting said lateral offset coupler to said spinal rod, said rod connector means including:

a connector having a one-piece body defining a rod channel adapted to receive said spinal rod therethrough, a stem bore adapted to slidably receive said elongated coupler stem therethrough and a threaded bore;

a threaded set screw adapted to be received within said threaded bore, wherein said stem bore has a length through said body and said rod channel intersects said stem bore along a portion of said length to permit contact between said rod and said coupler stem when the rod is received within said rod channel and the coupler stem is received within said stem bore, and further wherein, said threaded bore intersects one of said rod channel and said stem bore to permit contact between said set screw and one of said rod or said coupler stem when the set screw is threaded into the threaded bore, whereby said coupler stem is slidably received within said stem bore to position said offset body at variable lateral distances from said spinal rod, and further whereby said coupler stem and said rod are in clamped engagement when said set screw is threaded into said threaded bore to restrain relative movement between said rod and said fixation element.

2. The spinal implant system of claim 1, wherein said coupler stem includes a face disposed adjacent said rod when said coupler stem is received within said stem bore, said face of said coupler stem defining a groove extending along said length of said coupler stem, said groove forming opposite groove tips which engage said spinal rod.

3. The spinal implant system of claim 2, wherein:

said spinal rod includes a spiral groove defined along a substantial portion of the length of the rod; and said groove tips of said coupler stem are sized to be received within said spiral groove of said rod to restrain movement of said coupler stem along the length of said rod.

4. The spinal implant system of claim 2, wherein:

said threaded bore intersects said stem bore to permit contact between said set screw and said coupler stem when the set screw is threaded into the threaded bore and the coupler stem is received within said stem bore;

said coupler stem includes a second face disposed adjacent said set screw, said second face defining a second groove extending along the length of said coupler stem; and said set screw includes a curved tip configured to seat within said groove in said second face.

5. The spinal implant system of claim 1, further comprising means for temporarily fastening said lateral offset coupler to said rod connector means including:

said coupler stem having a stem length substantially greater than said length of said stem bore, a portion of said stem length including external threads; and a threaded nut for removably engaging said external threads of said portion of said stem length when said coupler stem extends through said stem bore of said rod connector means.

6. The spinal implant system of claim 1, wherein said means for engaging one of said number of fixation elements is generally perpendicularly offset from said coupler stem to permit superior/inferior offset of the fixation element when said lateral offset coupler is connected to said spinal rod.

7. A spinal implant system for correcting spinal deformities and abnormalities, comprising:

a first elongated spinal rod configured to be implanted adjacent the spinal column of a patient spanning across several vertebral levels;

a second elongated spinal rod configured to be implanted adjacent the spinal column on the opposite side of the spinous process from said first spinal rod;

a number of fixation elements for engaging vertebra at a number of vertebral levels, each of said number of fixation elements having a vertebra engaging portion;

means for connecting each of said fixation elements to a corresponding one of said first and second spinal rods when the fixation elements are engaged to a vertebra;

transverse connector means for connecting said first and second spinal rods including a transverse stem having a length sufficient to span between the two rods and having first and second ends; and a pair of rod connector means for connecting said transverse connector means to each of said spinal rods at each of said first and second ends, each of said rod connector means including:

a connector having a one-piece body defining a rod channel adapted to receive one of said spinal rods therethrough, a stem bore adapted to slidably receive said transverse stem therethrough, and a threaded bore;

a threaded set screw adapted to be received within said threaded bore, wherein said stem bore has a length through said body and said rod channel intersects said stem bore along a portion of said length to permit contact between said rod and said transverse stem when the rod is received within said rod channel and the transverse stem is received within said stem bore, and further wherein, said threaded bore intersects one of said rod channel and said stem bore to permit contact between said set screw and one of said spinal rods or said transverse stem when the set screw is threaded into the threaded bore, and said transverse stem is slidably received within said stem bore to adjustably span across variable distances separating said first and second spinal rods, and whereby said transverse stem and each of said spinal rods are in clamped engagement when said set screw of each of said pair of rod connector means is threaded into said threaded bore to restrain relative movement between said rod and said fixation element.

8. The spinal implant system of claim 7, wherein said transverse connector means includes a head formed at said first end of said transverse stem, said head being sized to prevent passage through said stem bore of one of said rod connector means.

9. The spinal implant system of claim 8, wherein:

said transverse stem has a length greater than the span between the two spinal rods, said transverse stem having external threads formed along a portion of said transverse stem from said second end of said transverse stem; and a threaded nut for removably engaging said external threads of said portion of said stem when said transverse stem extends through the stem bore of each of said pair of rod connector means.

10. The spinal implant system of claim 7, wherein said screw has an oval tip, and said transverse connector means includes a face defining grove configured for engagement by said oval tip.

11. The spinal implant system of claim 7, wherein stem bore is generally perpendicular to said threaded bore.

12. The spinal implant system of claim 7, wherein each of said rod connector means defines a rod opening intersecting said rod channel, said rod opening being configured to correspondingly receive one of said first and second elongated spinal rods therethrough to corrspondingly engage said rod channel.

13. A spinal implant system for correcting spinal deformities and abnormalities, comprising:

an elongated first spinal rod configured to be implanted adjacent the spinal column of a patient spanning across several vertebral levels;

at least a pair of fixation elements for engaging a vertebra at a number of vertebral levels, each of said pair of fixation elements having a vertebra engaging portion and an elongated stem extending from said vertebra engaging portion;

rod connector means for connecting said pair of fixation elements to said first spinal rod, said means including:

a connector having a one-piece body defining a rod channel adapted to receive said first spinal rod therethrough, a pair of substantially parallel stem bores adapted to receive said elongated stem of each of said pair of fixation elements therethrough, and a pair of threaded bores corresponding with said pair of stem bores; and a pair of set screws adapted to be received within a corresponding one of said pair of threaded bores, wherein each of said stem bores has a length through said body and said rod channel intersects each of said stem bores along a portion of said length to permit contact between said rod and a corresponding one of said elongated stems when said first spinal rod is received within said rod channel and the pair of stems are received within said pair of stem bores, and further wherein, each of said threaded bores intersects one of said rod channel and a corresponding one of said stem bores to permit contact between said set screw and one of said first spinal rod or said stem when the set screw is threaded into each said threaded bore, whereby said stems of said pair of fixation elements and said first spinal rod are in clamped engagement when said pair of set screws is threaded into corresponding ones of said threaded bores to restrain relative movement between said rod and said pair fixation elements, and between said pair of fixation elements relative to the other.

14. The spinal implant system of claim 13, wherein said vertebra engaging portion of each of said pair of fixation elements includes a hook.

15. The spinal implant system of claim 13, further comprising:

an elongated second spinal rod spaced apart from said first spinal rod;

a first rod fastener configured for connection to said first spinal rod;

a second rod fastener configured for connection to said second spinal rod; and a transverse connector having a first end portion opposite a second end portion, said first end portion being configured for attachment to said first rod fastener and said second end portion being configured for attachment to said second rod fastener.

16. The spinal implant system of claim 13, wherein said elongated stem defines a groove configured to engage said first spinal rod.

17. The spinal implant system of claim 13, further comprising:

an elongated second spinal rod spaced apart from said first spinal rod; and a number of vetebral engaging elements fixing for said second spinal rod to the spinal column of a patient.

18. The spinal implant system of claim 13, wherein said pair of stem bores are generally perpendicular to said rod channel.

19. The spinal implant system of claim 13, wherein said rod connector means defines a rod opening intersecting said rod channel, said rod opening being configured to receive said first spinal rod therethrough for placement in said rod channel.

20. The spinal implant system of claim 13, wherein each of said pair of set screws has an oval tip and each of said elongated stems defines a groove configured for engagement by said oval tip.

* * * * *